(12) United States Patent
Blagojevic et al.

(10) Patent No.: US 9,846,143 B2
(45) Date of Patent: Dec. 19, 2017

(54) ION MOBILITY METHOD AND APPARATUS (71) Applicants: DH Technologies Development PTE Ltd., Singapore (SG); Voislav Blagojevic, Toronto (CA); Diethard Bohme, Concord (CA)

(72) Inventors: Voislav Blagojevic, Toronto (CA); Diethard Bohme, Concord (CA); Thomas R. Covey, Newmarket (CA); Bradley B. Schneider, Bradford (CA)

(73) Assignee: DH Technologies Development Pte. Ltd., Singapore (SG)

( * ) Notice: Subject to any disclaimer, the term of this patent is extended or adjusted under 35 U.S.C. 154(b) by 0 days.

(21) Appl. No.: 15/438,986

(22) Filed: Feb. 22, 2017

(65) Prior Publication Data

US 2017/0219525 A1    Aug. 3, 2017

Related U.S. Application Data (62) Division of application No. 14/911,582, filed as application No. PCT/IB2014/001540 on Aug. 14, 2014, now abandoned.

(60) Provisional application No. 61/865,911, filed on Aug. 14, 2013.

(51) Int. Cl.
*H01J 49/00*    (2006.01)
*G01N 27/62*    (2006.01)

(52) U.S. Cl.
CPC .................. *G01N 27/624* (2013.01)

(58) Field of Classification Search
None
See application file for complete search history.

(56) References Cited

U.S. PATENT DOCUMENTS

| | | | |
|---|---|---|---|
| 6,331,710 B1* | 12/2001 | Wang | G02B 13/143 250/492.2 |
| 7,248,667 B2* | 7/2007 | Weiss | B82Y 10/00 250/492.2 |
| 2004/0051954 A1* | 3/2004 | Bristol | G02B 5/1838 359/634 |
| 2005/0230616 A1 | 10/2005 | Cameron et al. | |
| 2008/0149824 A1 | 6/2008 | Miller et al. | |
| 2008/0234945 A1 | 9/2008 | Walk et al. | |
| 2010/0149548 A1* | 6/2010 | Shmarev | G01N 21/95607 356/517 |
| 2010/0282966 A1 | 11/2010 | Schneider | |

(Continued)

FOREIGN PATENT DOCUMENTS

JP    2012-525672 A    10/2012

OTHER PUBLICATIONS

International Search Report and Written Opinion for PCT/IB2014/001540 dated Dec. 1, 2014.

(Continued)

*Primary Examiner* — Andrew Smyth (57) ABSTRACT

A method and system for performing an ion mobility based analysis that ionizes the components of a sample into ions; provides a field asymmetric waveform ion mobility or differential mobility spectrometry ion mobility based filter that comprises at least two electrodes, the at least two electrodes being spaced apart such that a constant sized gap is formed there between, through which a drift gas flows; introducing said ions into the drift gas, wherein said drift gas also comprises a mixture of liquid modifiers.

8 Claims, 10 Drawing Sheets

(56) References Cited

U.S. PATENT DOCUMENTS

| | | |
|---|---|---|
| 2011/0300638 A1 | 12/2011 | Atkinson |
| 2012/0044473 A1* | 2/2012 | Lippert .................. G02B 1/10 355/66 |
| 2013/0062517 A1 | 3/2013 | Shvartsburg |

OTHER PUBLICATIONS

Voislav Blagojevic et al. "Differential Mobility Spectrometry of Isomeric Protonated Dipeptides: Modifier and Field Effects on Ion Mobility and Stability" Anal. Chem., 2011. 83(9). pp. 3470-3476.
Roberto F.M. et al. "Buffer gas modifiers effect . . . clustering reactions" Rapid Commun. Mass Spectrom. 2012, 26.2211-2223 (Sep. 6, 2012) See the whole document.

\* cited by examiner

ION MOBILITY METHOD AND APPARATUS

RELATED APPLICATION

This application is a divisional of U.S. application Ser. No. 14/911,582, filed on Feb. 11, 2016, which claims the benefit of priority from U.S. Provisional Application Ser. No. 61/865911, filed on Aug. 14, 2013, the contents of which are incorporated by reference.

FIELD

The present teachings relate to the use of modifiers in differential mobility spectrometers and field asymmetric waveform ion mobility spectrometers.

BACKGROUND

A Differential Mobility Spectrometer (DMS) system typically performs a gas phase ion sample separation and analysis. It operates with an asymmetric waveform alternating between high and low field conditions, and includes the use of at least two parallel electrode plates separated by a constant sized gap. A similar, but related system that also uses asymmetric waveforms is the Field Asymmetric Waveform Ion Mobility Spectrometer (FAIMS) which typically describes the use of a cylindrical configuration which includes an inner and an outer electrode, separated by a constant sized gap. In some circumstances, both DMS and FAIMS devices have been interfaced with a mass spectrometer (MS) to take advantage of the atmospheric pressure, gas phase, and continuous ion separation capabilities of the DMS/FAIMS and the detection accuracy of the MS.

By interfacing a DMS/FAIMS with an MS, numerous areas of sample analysis, including proteomics, peptide/protein conformation, pharmacokinetic, and metabolism analysis have been enhanced. In addition to pharmaceutical and biotech applications, DMS-based analyzers have been used for trace level explosives detection and petroleum monitoring.

A DMS/FAIMS, like an ion mobility spectrometer (IMS), is considered an ion mobility based analyzer because the DMS/FAIMS/IMS separates and analyzes ions based on the mobility characteristics of the ions. In an IMS, ions are pulsed into and pass through a drift tube while being subjected to a constant electric field. The ions interact with a drift gas in the drift tube and the interactions affect the time it takes for the sample ions to pass through the drift tube, e.g., the drift time. These interactions are specific for each analyte ion of a sample, leading to an ion separation based on more than just mass/charge ratio. In contrast, in a TOF MS, there is a vacuum in the drift region of the MS and, therefore, an ion's time through the MS drift region is based on the ion's mass-to-charge ratio (m/z) in the collision-free environment of the vacuum.

A DMS/FAIMS is similar to an IMS in that the ions are separated in a drift gas. However, unlike an IMS, the DMS/FAIMS uses an asymmetric electric field waveform that is applied between at least two parallel electrodes through which the ions pass, typically, in a continuous manner. The electric field waveform typically has a high field duration at one polarity and then a low field duration at an opposite polarity. The duration of the high field and low field portions are applied such that the net voltage being applied to the DMS/FAIMS filter electrodes is zero. While certain figures and embodiments herein described pertain specifically to DMS devices, it would be appreciated by the skilled person that a FAIMS device could also be utilized to carry out a similar procedure with modification where appropriate.

Figure 1A:
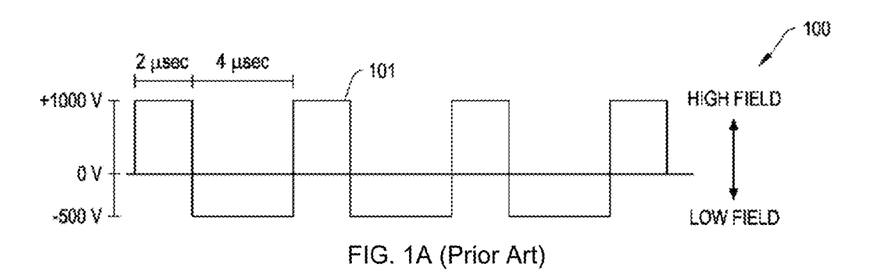
FIG. 1A includes an illustration of the high and low voltages of opposite polarity applied to generate the asymmetric electrical waveform and FIG. 1B depicts a conceptual diagram of a DMS filter where the path of an ion $M^+$ is subject to an asymmetric field resulting from the asymmetric waveform.
Figure 1B:
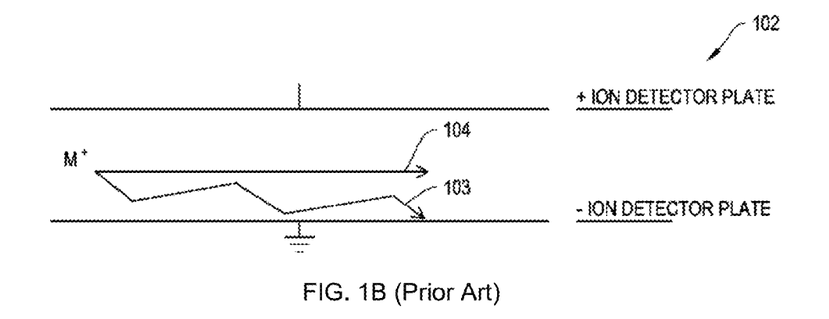
Figure 2:
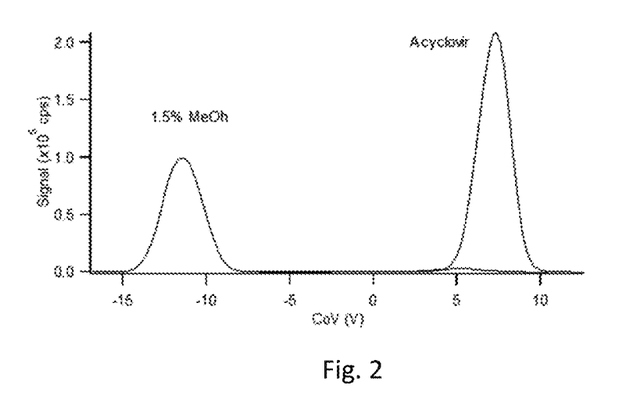
FIG. 2 is a superimposed ionogram for the compound acyclovir with and without the use of a chemical modifier.
Figure 3:
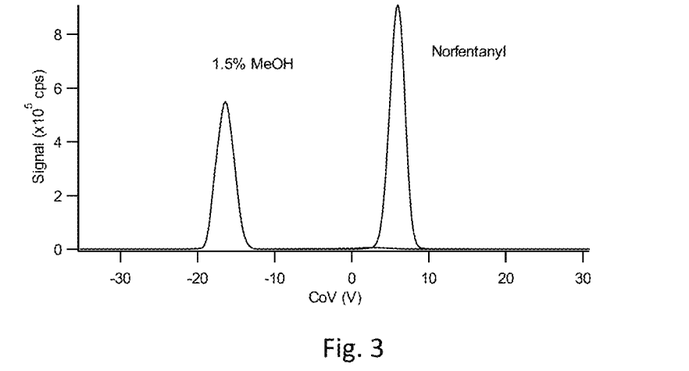
FIG. 3 is a superimposed ionogram for the compound norfentanyl with and without the use of a chemical modifier.
Figure 4:
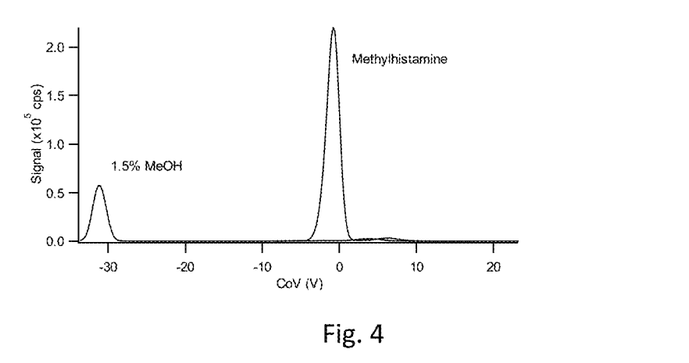
FIG. 4 is a superimposed ionogram for the compound methylhistamine with and without the use of a chemical modifier.
Figure 5:
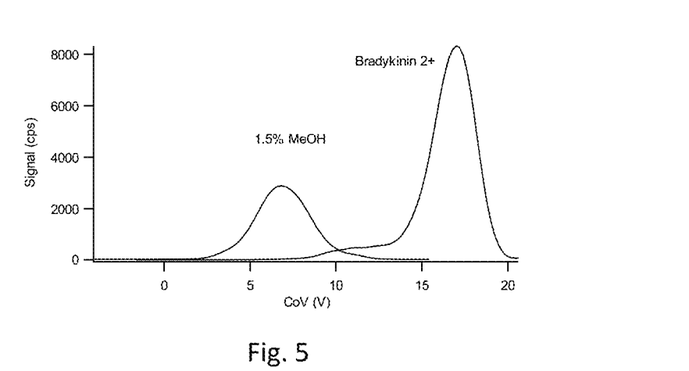
FIG. 5 is a superimposed ionogram for the peptide bradykinin with and without the use of a chemical modifier.

FIG. 1A shows a plot 100 of one variant of the time-varying, RF, and/or asymmetric high and low voltage waveform 101 (e.g., Vrf) that can be applied to generate an asymmetric electric field. FIG. 1B shows a diagram of a DMS filter 102 where the path of an ion $M^+$ is subjected to an asymmetric electric field resulting from the asymmetric voltage waveform 101. This ion can also be multiply charged. The ion's mobility in the asymmetric electric field indicates a net movement 103 towards the bottom electrode plate of the DMS filter 102. This example shows that, in a DMS, an ion's mobility is not constant under the influence of the low electric field compared to the high electric field. Since an ion may experience a net mobility towards one of the filter electrode plates during its travel between the plates, a compensation voltage (Vc) is applied to the filter electrodes to maintain a safe trajectory 104 for the ion through the DMS filter 102 without striking one of the filter electrodes. The ions are passed between the two filter electrodes by either being pushed through with a pressurized gas flow upstream of the filter electrodes or pulled through by a pump downstream from the filter electrodes.

In a DMS or IMS, ions are typically separated in a gas at pressures sufficient to enable collisions between sample ions and neutral drift gas molecules. The smaller the ion, the fewer collisions it will experience as it is pulled through the drift gas. Because of this, an ion's cross sectional area can affect the ion's mobility through the drift gas. As shown in FIG. 1B, an ion's mobility may vary with electric field strength. This difference in mobility may be augmented by clustering/de-clustering reactions taking place as an ion experiences the weak and strong electric fields. An ion may experience clustering with neutral molecules in the drift gas during the weak field portion of the waveform, resulting in an increased cross sectional area. During the strong field portion of the waveform, the cluster may be dissociated, reducing the ion's cross sectional area. Alternatively, differences between high and low field mobility behavior may be due to different collision dynamics due to changes that occur in ion translational energy, such as polarization effects.

The integration of a DMS with a MS can provide added selectivity that can be used for purposes such as chemical noise reduction and elimination of isobaric interferences. This general reduction of the chemical background can provide improvements in the detection limit (defined for example as 3 σ/slope of the calibration curve) for various assays. One of the key factors limiting general applicability of DMS technology with MS analysis is the reduction in instrument sensitivity that is observed upon installation of the DMS. These sensitivity reductions may occur as a result of many different phenomena, including: 1) diffusion losses in the DMS itself, 2) inefficiencies in ion transport into and out of the DMS, and 3) ion clustering. It is believed that some of the losses currently being observed with the DMS at high solvent flows are a result of sampling a "wet spray" into the DMS and subsequently filtering clusters that do not transmit at the same Vc as the unclustered parent ion. This hypothesis is supported by modeling of diffusion behavior, as well as experimental data showing improvements in the coefficient of transmission with additional heaters located in front of the DMS.

In existing DMS-MS systems, there are several approaches where desolvation or declustering are utilized including: 1) the source region where turbo heaters can be operated up to 750° C., 2) a counter-current gas flow region established by the heated curtain gas, and 3) a declustering region within the first vacuum stage where the potential difference between the inlet orifice and first vacuum lens element provides some declustering. Existing DMS-MS systems typically locate the DMS before the orifice of the MS, which results in a limitation in that ions and clusters are filtered prior to the orifice, eliminating the ability to decluster within the first vacuum stage. Elimination of this stage of declustering may result in sensitivity reduction with the DMS, with higher solvent flows being most problematic. Efforts to add additional heating and provide additional desolvation prior to the DMS have shown some improvement in sensitivity, however, they have imparted very significant challenges with respect to commercialization due to the critical importance of maintaining a constant temperature and the difficulty of monitoring temperature in close proximity to very high AC potentials. The range of assays that can exhibit detection limit improvements with the DMS is limited by the magnitude of the sensitivity reduction that is observed with the DMS device.

Improvements in resolution in the DMS can be made by adding a modifier liquid to the drift gas. Modifiers can provide selectivity by clustering with ions to varying degrees, which can shift the differential mobility properties of the resulting ions. The liquid modifiers can include a wide ranging field of solvents, including alcohols-such as 2-propanol, water, as well as hydrogen and deuterium exchange agents (such as $D_2O$ or $CH_3OD$). However, the introduction of a modifier has often resulted in a decrease in sensitivity which leads to a loss or reduction in signal intensity. Representative examples of such a phenomenon are depicted for various samples in FIGS. 2 to 5. Additionally, stability issues have been noted when using very small flow rates for liquid modifiers.

Accordingly, there is a need to improve mobility based resolution and specificity, and to increase the applicability of DMS type analyses by providing improved sensitivity and selectivity, including for high flow analyses.

SUMMARY

The use of liquid modifiers in mobility based analyzers such as a DMS, has been found to decrease the level of signal that is detected. It has been unexpectedly found that it is possible to gain back some, and in some cases, even all of the lost signal by introducing additional liquid modifiers. Thus, instead of a single liquid modifier, a mixture of two or more liquid modifiers is added to the drift gas stream.

While not wishing to be bound by theory, it is believed that the initial loss of signal due to the use of a single modifier is due to premature fragmentation or proton transfer from the ion of interest to the modifier. The proton transfer problem can be exacerbated when using high proton affinity modifiers with low proton affinity analytes, which can culminate in the complete loss of usable signal. The use of a solvation modifier that has a lower proton affinity than that of the analyte of interest can assist in preventing proton transfer from the analyte ion. The modifier, when present in a solvating capacity, can also protect the analyte of interest from fragmentation by consuming some of the collision energy through desolvation, and/or reducing the overall mobility.

In various embodiments, the within teachings describe a method of performing an ion mobility based analysis comprising ionizing the components of a sample into ions; providing a field asymmetric waveform ion mobility or differential mobility spectrometry ion mobility based filter that comprises at least two electrodes, the at least two electrodes being spaced apart such that a constant sized gap is formed there between, through which a drift gas flows; introducing the ions into the drift gas, wherein the drift gas also comprises a mixture of liquid modifiers, the mixture comprising: a first solvent to improve the separation capability of the drift gas; a second solvent to suppress either proton transfer or analyte dissociation of the ions, the second solvent having a higher proton solvation energy than that of the first solvent, and being added in excess to that of the first solvent; and detecting the ions after they have passed through the drift gas.

In various embodiments, the first solvent is selected to cluster with the ions.

In other embodiments, the first solvent is selected from a group consisting of C1-C10 alcohols, nitrile solvents, halogenated solvents and non-alcohol hydrocarbon based solvents.

In various embodiments, the first solvent is hexanol.

In various embodiments, the second solvent is selected from a group consisting of C1-C10 alcohols, nitrile solvents, halogenated solvents and non-alcohol hydrocarbon based solvents.

In various embodiments, the second solvent is methanol.

In various embodiments, the mixture further comprises a third solvent that is an arcing suppressant modifier In various embodiments, the arcing suppressant modifier is an electron accepting modifier.

In various embodiments, the arcing suppressant modifier is non-polar.

In various embodiments, the arcing suppressant modifier is chloroform.

In various embodiments, the sample comprises a protein, a peptide, an amino acid, or a mixture thereof.

In various embodiments, the sample is comprised of small molecules.

In various embodiments, the second solvent is added at least 2 times in excess of the first solvent.

In various embodiments, the second solvent is added at least 6 times in excess of the first solvent.

In various embodiments, the within teachings describe an ion mobility analysis system comprising: a differential ion mobility or field asymmetric waveform based filter having at least two electrodes spaced apart from one another to form a constant sized gap there between, a drift gas supply for introducing a drift gas into the ion mobility based filter; a liquid modifier supply for introducing a liquid modifier into the drift gas, the liquid modifier supply comprising at least two different liquid solvents and an ion detector.

In various embodiments, the two different liquid solvents comprise a first solvent to improve the separation capability of said drift gas; a second solvent to suppress either proton transfer or analyte dissociation, the second solvent having a higher proton solvation energy than that of the first solvent, and being present in excess to that of the first solvent when the liquid modifier enters said drift gas supply.

In various embodiments, the liquid modifier comprises a third solvent wherein said third solvent is an arcing suppressant modifier.

In various embodiments, the first solvent is hexanol and the second solvent is methanol.

In various embodiments, the arcing suppressant modifier is chloroform.

In various embodiments, the within teachings describe a method of improving the sensitivity in a differential mobility or field asymmetric ion mobility analysis system that utilizes a chemical modifier to improve selectivity of ions in a sample, the method comprising administering a solvation modifier in connection with the chemical modifier, wherein the solvation modifier has a higher proton solvation energy and is added in excess to that of the chemical modifier.

In various embodiments, the solvation modifier also has a lower proton affinity than that of the ions in the sample.

In various embodiments, the arcing suppressant modifier is added in connection with the chemical and solvating modifiers.

In various embodiments, the within teachings describe a method of improving the selectivity in a differential mobility or field asymmetric ion mobility analysis system, the method comprising administering an arcing suppressant modifier that scavenges electrons and allows the system to operate at a higher separation voltage than is possible without the use of the arcing suppressant modifier.

DESCRIPTION OF VARIOUS EMBODIMENTS

While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

The mixture of liquid modifiers can include one or more primary separation modifiers which function to separate different ion components while passing through the drift gas of a DMS device. This manifests itself as the resolving of peaks in a derived analysis spectrum. Exemplary solvents for such purposes can include a C1 to C10 alcohol and can in particular include hexanol, octanol, isopropanol, methanol and the like or can include other types of solvents such as nitrile solvents, including but not limited to acetonitrile or propionitrile. Reference to C1 to C10 alcohols includes the use of alcohols containing between 1 and 10 carbons. The carbons can exist as straight chains or can be branched or cyclic. Other types of solvents may also be utilized including halogenated type solvents which include, but are not specifically limited to such solvents such as chlorobenzene, carbon tetrachloride, chloroform, and dichloromethane and the like. In addition, other non-alcohol hydrocarbon based solvents may also be utilized, including, but not limited to, ethylacetate, acetone, cyclohexane and the like. In some cases, the separation modifier is polar in nature. It may also be advantageous to further include a secondary "separation modifier" which is different from the primary separation modifier. The secondary separation modifier can be selected from the same types of solvents that are the primary modifier and can include alcohols, such as the C1 to C10 alcohols or other types of solvents such as nitrile solvents including, acetonitrile or propionitrile, the halogenated solvents and the non-alcohol hydrocarbon based solvents described above.

The mixture of liquid modifiers can also include a solvating modifier that assists in suppressing proton transfer or analyte dissociation. The solvating modifier is typically added in excess to that of the separation modifier in order to ensure that the analyte ion is solvated before encountering the separation modifier molecule. Solvation of the analyte ion increases its effective proton affinity by the value of solvation energy and makes proton transfer less favourable. Determining whether a solvent is a suitable solvating modifier can be made by looking at the energy of sequential solvation of the protonated analyte. Typically, the lower (or more negative) the solvation energy, the more beneficial the solvent is as a solvation modifier. A low solvation energy typically results in a high solvation reaction rate with the analyte ion, reducing the likelihood of the encounter of a desolvated analyte ion with the separation modifier. A low solvation energy also makes proton transfer reactions thermodynamically less favourable as it leads to a larger increase in the effective proton affinity of the analyte ion. Additionally, the solvating modifier may have a low proton affinity, which minimizes the possibility of proton transfer. Preferably, the proton affinity will be less than the proton affinity of the analyte of interest. Examples of such solvating modifiers include water and/or methanol when used with an appropriate separation modifier. The solvation modifier may also include, when used with an appropriate separation modifier, a C1 to C10 alcohol which can in particular include hexanol, octanol, isopropanol, methanol and the like or can include other types of solvents such as nitrile solvents, including but not limited to acetonitrile or propionitrile. Other types of solvents may also be utilized as solvation modifier, when used with an appropriate separation modifier and can include halogenated type solvents which include, but are not specifically limited to such solvents such as chlorobenzene, carbon tetrachloride, chloroform, and dichloromethane and the like. In addition, other non-alcohol hydrocarbon based solvents may also be utilized as the solvation modifier, when used with an appropriate separation modifier and can include ethylacetate, acetone, cyclohexane and the like. Proton solvation energies for a number of exemplary solvents can be obtained from various texts in the art. Exemplary solvation energies from the NIST Chemistry Webbook are depicted in Table 1 which shows the solvation energies for the reaction of a solvent molecule to a solvated proton already solvated by n solvent molecules according to the following equation.

$$H^+(\text{solvent molecule}) \times n + (\text{solvent molecule}) \rightarrow H^+ (\text{solvent molecule}) \times (n+1)$$

TABLE 1

Enthalpies of protonation (n = 0) and solvation (n > 0) in kcal/mol for various liquid modifiers. Solvation energy for cyclohexane is for solvation of ammonium ion. This data is available in the NIST Chemistry WebBook as a part of the Reaction Thermochemistry Database.

| n | water | methanol | ethanol | isopropanol | Butanol | pentanol | Cyclohexane |
|---|---|---|---|---|---|---|---|
| 0 | −165.1 | −180 | −185.6 | −189.5 | −188.6 | −190 | −164.5 |
| 1 | −32 | −32.6 | −32.1 | −31.9 | −31.5 | | −9 |
| 2 | −20 | −21.2 | | | | | |
| 3 | −17.3 | −16.1 | | | | −22 | |
| 4 | −13.4 | −13.5 | | | | −14 | |
| 5 | −12 | −12.5 | | | | −12 | |
| 6 | −10.7 | −11.9 | | | | −11 | |
| 7 | −10.3 | −12 | | | | | |

Proton affinity of the solvents are also available from the above table and are equal to the positive value of the n=0 enthalpy (ie, proton affinity values are positive).

In addition to suppressing proton transfer between the analyte ion and the separation modifier, the solvation modifier can also reduce the extent of analyte ion fragmentation caused by the electric field in the DMS. Due to the presence of charge, analyte ions are accelerated upon entering the DMS by the applied separation AC potential. This leads to collisions with the nitrogen and modifier molecules that result in deposition of internal energy in the analyte ion. Higher separation AC potential will increase the amount of energy deposited in the analyte ion, leading to eventual ion fragmentation and signal loss. The presence of the solvating modifier changes the rate of energy deposition. When the solvated analyte ion is subjected to collisions with nitrogen and modifier molecules a portion of the energy, instead of being deposited as the internal energy of the analyte ion, is used to desolvate the ion. The solvation/desolvation process occurs continuously as the analyte ion travels through the DMS, leading to a lower rate of internal energy deposition and a lower likelihood of fragmentation for the analyte ion. While this process is generally applicable to any modifier in the DMS, the same traits that make a molecule a desirable solvation modifier, such as low solvation energy, which increases the rate of solvation, also lowers the rate of internal energy deposition through collisions. Additionally, a solvation modifier may decrease the rate of analyte ion heating by reducing the ion mobility and hence internal energy input.

When utilized on its own, the use of a separation modifier typically will result in a decrease in signal intensity. FIGS. 2 to 5 show DMS ionographs of acyclovir, norfentanyl, methylhistamine and bradkykinin, respectively, measured using pure nitrogen gas as a transport gas without a modifier added superimposed on an ionograph of the same compound measured with a single 1.5% methanol modifier. This data was acquired on a commercial SelexION 5500 QTRAP type device. The shift in Compensation Voltage (Vc) as well as the reduction in sensitivity (i.e., signal intensity) is clearly evident when a single separation modifier is used.

When using a suitable separation modifier for a particular analyte sample, reductions in signal intensity in the DMS caused by the addition of the modifier can be mitigated by the addition of an additional solvent, the solvation modifier that is added in sufficient amount to make the rate of reaction of the analyte ion with the solvating modifier much higher than the rate of reaction with the separation modifier. In some embodiments this is achieved by having a solvating modifier with lower solvation energy than the separation modifier. In some embodiments, it is advantageous that the solvation modifier is highly polar (high dipole moment and polarizability), giving it a much higher collision rate with the analyte ion than the separation modifier. In some embodiments, it is also advantageous if the solvation modifier is added in excess to that of the separation modifier. In some embodiments, the solvation modifier is added at least 2 times in excess, in other embodiments, the solvation modifier is added at least 6 times in excess. In some embodiments, the solvation modifier may also have a lower proton affinity than the separation modifier which prevents proton transfer to the modifier from the ion(s) of interest.

It may also be advantageous to include an arcing suppressant modifier which functions to reduce the probability of an electrical discharge from the electrodes which would otherwise affect the uniformity and stability of the generated electric fields. This allows the operation of the DMS with a higher separation voltage, which can also assist in resolving of peaks in the spectra. Typically, such an arcing suppressant modifier is a high electron affinity solvent that readily accepts electrons, and can include a relatively non-polar solvent such as chloroform. The arcing suppressant modifier will scavenge free electrons that are formed in the region between the DMS electrodes and prevent them from creating a cascade effect that may ultimately lead to an electric discharge (e.g. arcing) in the device. Any amount of solvent capable of accepting electrons is expected to reduce the concentration of free electrons, but typically smaller amounts of the arc suppressant modifiers are required. In some embodiments, the arc suppressant modifier is added in half the amount as the separation modifier.

The introduction of the drift gas into the DMS system can be made using the conventional known methods in the art. For example, referring to FIG. 14, which depicts a DMS in accordance with an embodiment of the present teachings coupled to a mass spectrometer 204a. The mass spectrometer 204a is disposed downstream from vacuum chamber 227 as a result of vacuum pump 230 with associated ion guide elements 204. The differential mobility spectrometer 202 can be contained within a curtain chamber 218 defined by a curtain plate or boundary member 219 and supplied with the curtain gas from the curtain gas supply 220 via curtain gas conduit 220a. When the curtain gas is released into the curtain chamber by the curtain gas conduit 220a, it can contain a quantity of modifier liquid mixture 214 that had previously been mixed. Ions 222 are provided from an ion source (not shown) and are emitted into the curtain chamber 218 via curtain chamber inlet 224. The pressure of the curtain gases in the curtain chamber 218 can be maintained at or near 760 Torr. This pressure can provide both a curtain gas outflow 226 out of curtain gas chamber inlet 224, as well as a curtain gas inflow 228 into the differential mobility spectrometer 202, which inflow 228 becomes the drift gas 208 that carries the ions 222 through the differential mobility spectrometer 202 and into the vacuum chamber 227 through the vacuum chamber inlet 229. As the curtain gas within the curtain chamber 218 can include the modifier liquid mixture 214, the drift gas 208 can also comprise the modifier liquid mixture. Optionally, the system 200 may comprise a mixing chamber instead of, or in addition to, the curtain chamber. This mixing chamber could be located in the curtain gas conduit 220a upstream from the differential mobility spectrometer. In such an embodiment, the mixing chamber could facilitate mixing of the modifier liquid mixture and the curtain gas. As is typically used in modifier delivery, the apparatus can contain heaters and/or other means to vapourize the modifier in accordance with the state of the art.

Figure 14:
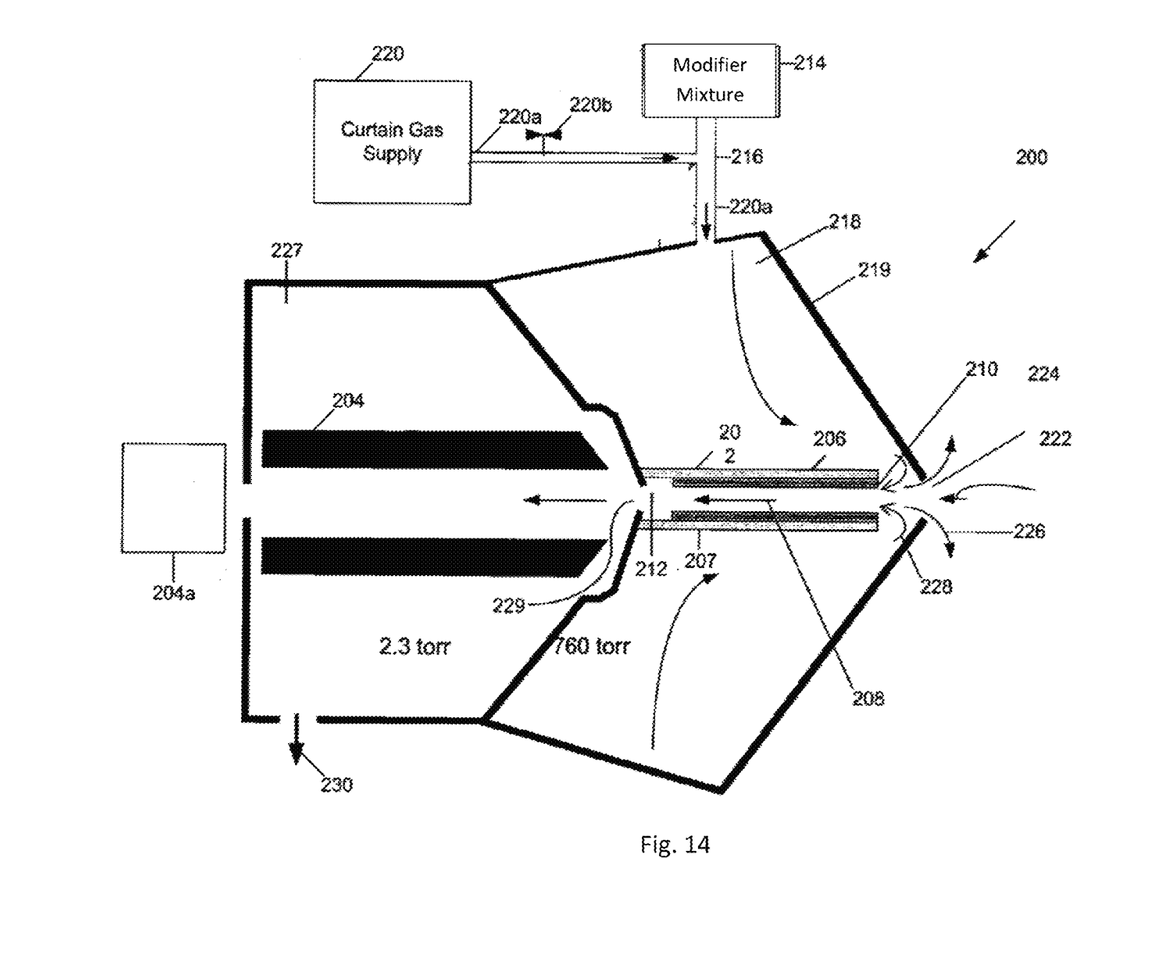
FIG. 14 is an illustration of a DMS and mass spectrometer in accordance with an embodiment.

While FIG. 14 specifically depicts the introduction of ions into a mass spectrometer through the use of an orifice, it would be appreciated by the skilled person that other methods of introducing ions into a mass spectrometer could also be used within the scope of the present teachings. For example, ions may also be introduced via a capillary tube or an ion pipe type system.

Figure 15:
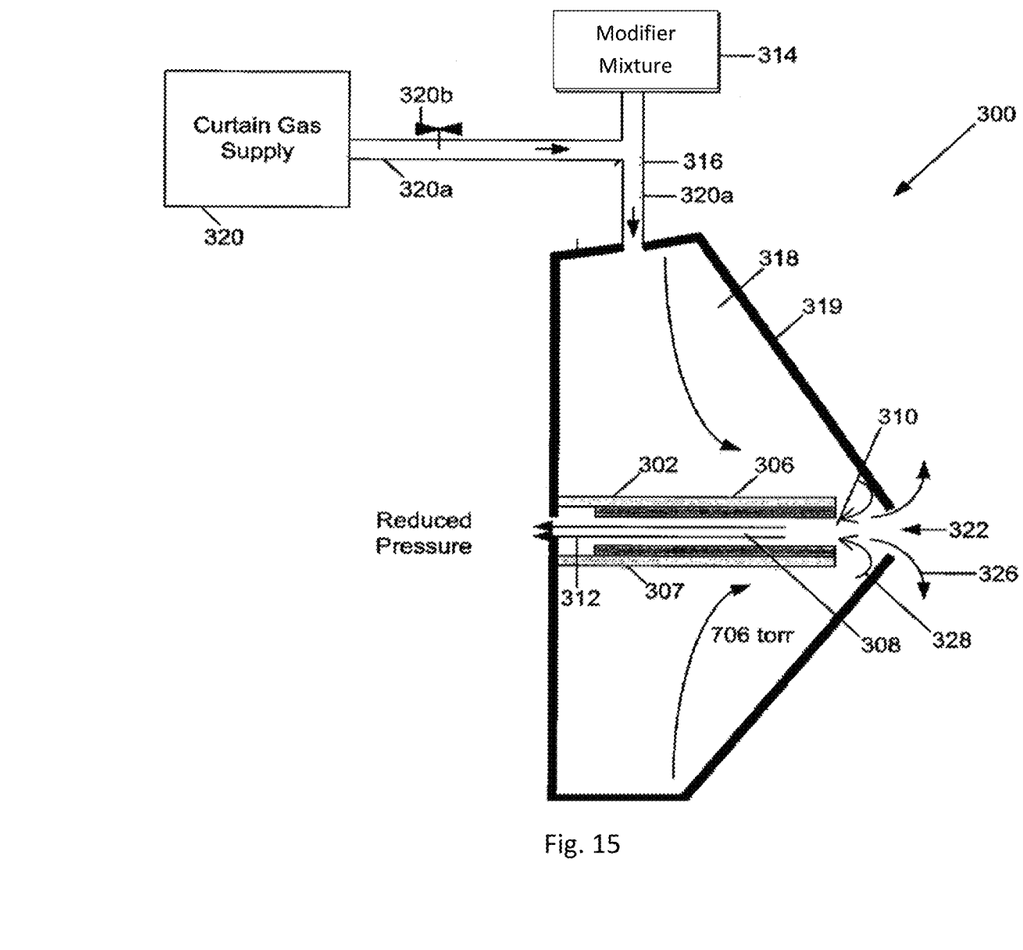
FIG. 15 is an illustration of a DMS in accordance with another embodiment.

As shown, the differential mobility spectrometer system 300 of FIG. 15 resembles a portion of the system 200 of FIG. 14, but lacks the mass spectrometer and vacuum chamber elements of FIG. 14. Accordingly, the differential mobility spectrometer 300 of FIG. 15 can be installed upstream of any number of different mass spectrometer elements, or may simply be installed upstream of a region of reduced pressure, as shown, which draws the ions 322 and drift gas 308 through the differential mobility spectrometer 302. Alternatively, there may be a detector downstream of the outlet of the differential mobility spectrometer 302 such as a Faraday cup or other ion current measuring device. The differential mobility spectrometer 302 is contained within a curtain chamber 318. The curtain chamber 318 is supplied with a curtain gas from a curtain gas supply 320 in a manner similar to that described above in connection with FIG. 14.

It would be appreciated by those in the art that while the liquid modifier mixture can be added to the system in the curtain gas, with a portion of it eventually becoming the drift gas, the liquid modifier mixture may also be added directly to the drift gas through appropriate means such as direct injection into the inlet 210 of the DMS. In this way, modifier liquid is not wasted in the curtain chamber or in the curtain gas outflow 226. The modifier mixture may also be provided at discrete modifier flows into the mixing chamber, curtain chamber, or gas conduits 220a. It would also be possible to split the curtain chamber into 2 discrete regions as described for example, in US Published Application No. 2013/0264493.

If the mixture of solvents is added to the drift gas as a mixture, it would be appreciated that the individual solvents being utilized should be miscible with one another. Solvents that are not miscible with one another can still be utilized in accordance with the present teachings if the solvents are introduced into the system separately for example by the use of separate streams through multiple injector sites. This can be achieved for example by the use of separate injection sites into the curtain gas for the different types of modifiers being used, or by having the multiple streams injected separately directly into the entrance of the DMS. In addition, as would be appreciated, even if solvents are miscible with one another, the solvent need not be premixed prior to their introduction into the drift gas. The solvents may be introduced separately into the drift gas or curtain chamber through, for example, separate injection sites.

The DMS system described herein is intended to include all types of devices which separate ions based on differential mobility based on the application of an asymmetric waveform. For example, the term DMS as described herein, is intended to include for example, FAIMS devices and micromachined DMS devices.

The present teachings can be utilized across a broad region of chemical space and can be utilized to increase separation and signal for a wide variety of molecules that can include proteins, peptides, amino acids and small molecules. In particular, molecules especially suited for the disclosed method are those in which ionization has resulted in the addition of a proton to the molecule to cause a net positive charge. In this manner, the high proton solvation energy of a solvent being used as a solvation modifier is able to solvate the proton and thus resulting protonated molecules. In particular, suitable types of molecules are particularly peptide sequences. Exemplified peptide sequences discussed herein include bradykinin and Bovine Serum Albumin (BSA) digest, though other peptide sequences should also benefit from the within teachings. Other suitable types of molecules include small molecules. Examples of such small molecules that can be used in connection with the present teachings include acyclovir, clenbuterol, clomipramine, desipramine, diphenylhydrazine, ketamine, maprotiline, minoxidil, methadone, methylhistamine, norfentanyl, penbutolol, pheniramine, propafenone, terbutaline or terfanadine and mixtures thereof.

EXAMPLES

Bradykinin

Bradykinin samples were analyzed in a DMS system, monitoring for the 2+ ion.

Figure 8:
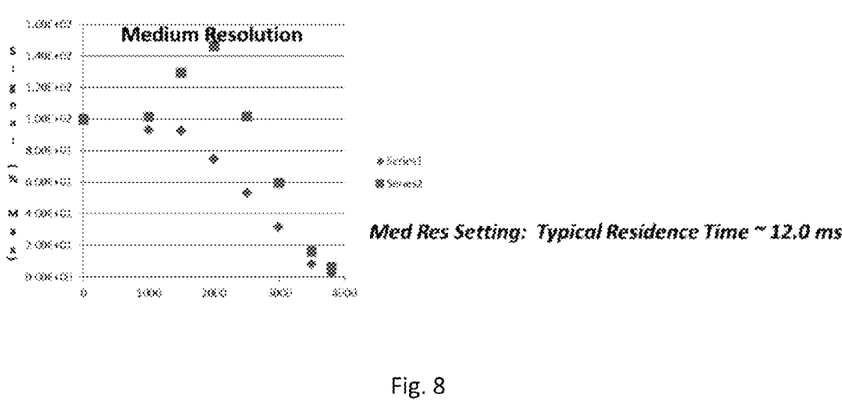
FIG. 8 is a plot of data taken at medium resolution for bradkykinin showing a single modifier and a mixture of modifiers.
Figure 9:
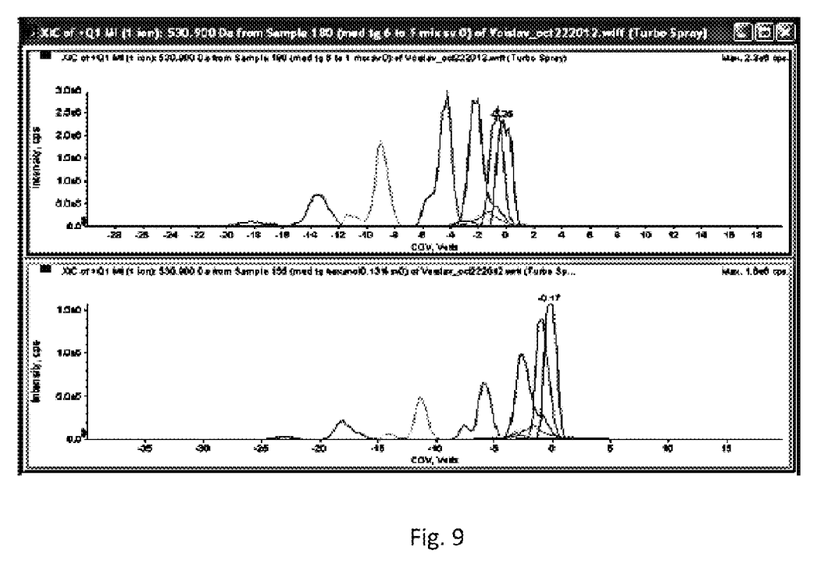
FIG. 9 is a medium resolution ionogram of bradkykinin showing a single modifier and a mixture of modifiers.
Figure 10:
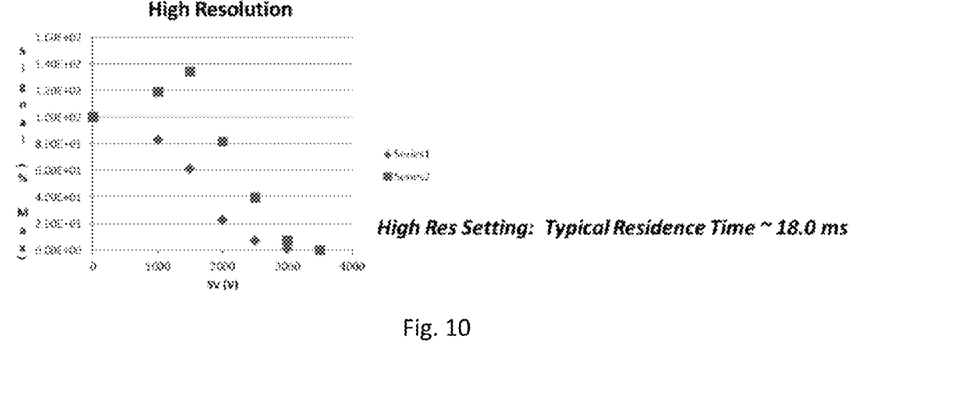
FIG. 10 is a plot of data taken at high resolution for bradkykinin showing a single modifier and a mixture of modifiers.
Figure 11:
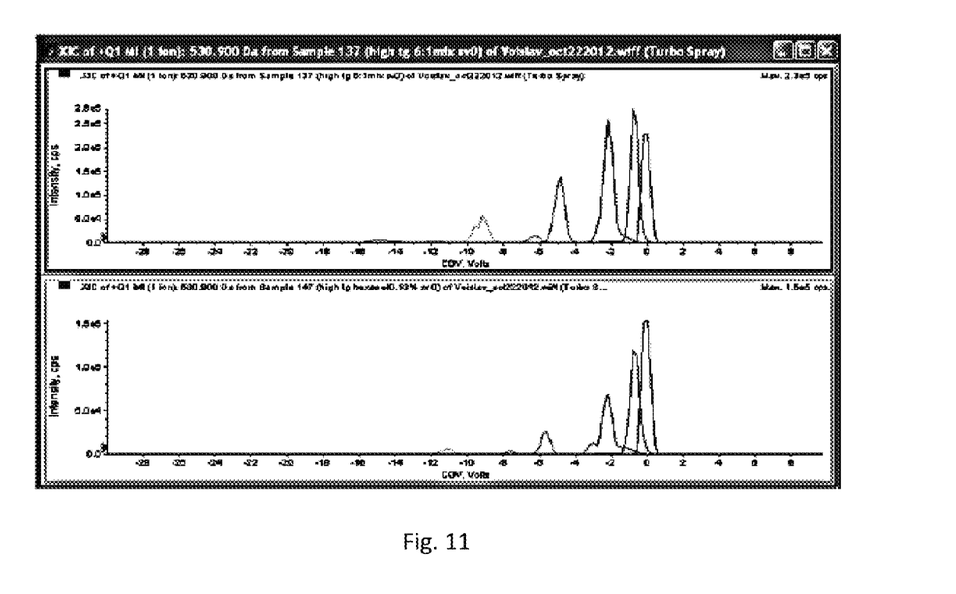
FIG. 11 is a high resolution ionogram of bradkykinin showing a single modifier and a mixture of modifiers.

FIGS. 6 to 11 show a series of data plots for bradykinin conducted at various residence times which include, low resolution-residence time of approximately 8.6 ms (FIGS. 6 and 7), medium resolution-residence time of approximately 12 ms (FIGS. 8 and 9) and high resolution-residence time of approximately 18 ms (FIGS. 10 and 11).

Figure 7:
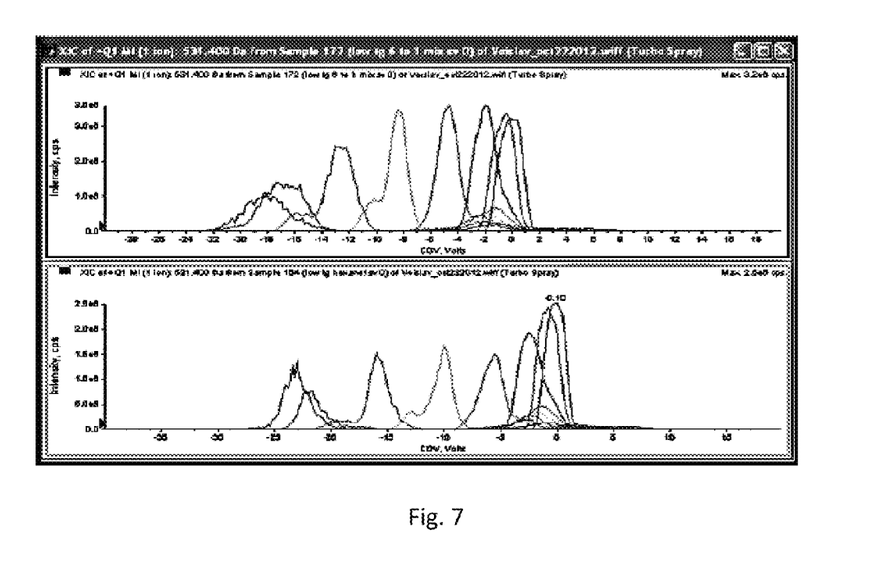
FIG. 7 is a low resolution ionogram of bradkykinin showing a single modifier and a mixture of modifiers.

For each of FIGS. 7, 9 and 11, ionograms for a hexanol modifier (bottom pane) and hexanol modifier mixture with 6× greater fraction of methanol modifier (top pane) are depicted with various separation voltage settings. The data presented in each are normalized to the bradykinin signal intensity from transparent mode. The signal for the peptide was higher for the separation voltage values when using the modifier mixture containing the 6-fold excess of methanol.

Figure 6:
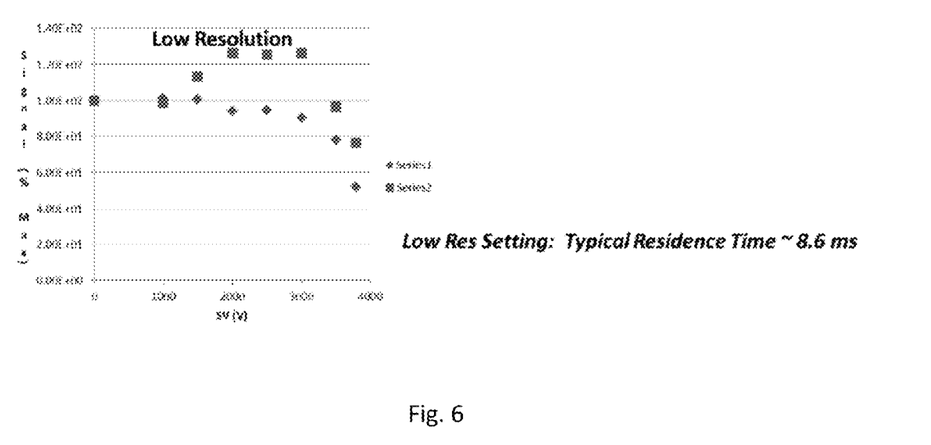
FIG. 6 is a plot of data taken at low resolution for bradkykinin showing a single modifier and a mixture of modifiers.

FIGS. 6, 8 and 10 show plots of intensity vs. separation voltage of an overlay of data using hexanol modifier (diamonds) and a hexanol modifier containing an excess of methanol (squares) for the low, medium and high resolutions, respectively. For FIG. 7, each of the peaks depicted in the ionogram corresponds to a point present in the plot depicted in FIG. 6. Similar relationships exist for the ionogram in FIG. 9 and the plot of FIG. 8 and the ionogram of FIG. 11 and the plot of FIG. 10.

These figures demonstrate that the addition a solvating modifier such as methanol can improve the ion transmission when using a separation modifier such as hexanol. These results are surprising because as seen in FIGS. 2 to 5, and more particularly in FIG. 5, when methanol is utilized on its own as a modifier, the intensity of the signal tends to decrease. With the use of methanol however as a second solvating modifier in addition to the use of the separation modifier hexanol, it was unexpectedly found to restore signal. Signal loss effects with increasing separation voltage were the worst when running with longer residence times. The addition of a 6-fold excess of methanol helped to reduce the losses. The extent of the improvement increases dramatically as the residence time within the DMS increases.

TABLE 2

Low Resolution (residence time = approx. 8.6 ms)

| SV(V) | Hexanol (Counts/sec) | Hexanol + MeOH (Counts/sec) | Gain with addition of MeOH |
|---|---|---|---|
| 0 | $5.32 \times 10^6$ | $6.83 \times 10^6$ | X 1.28 |
| 1000 | $5.39 \times 10^6$ | $6.73 \times 10^6$ | X 1.25 |
| 1500 | $5.37 \times 10^6$ | $7.75 \times 10^6$ | X 1.44 |
| 2000 | $5.02 \times 10^6$ | $8.63 \times 10^6$ | X 1.72 |
| 2500 | $5.03 \times 10^6$ | $8.58 \times 10^6$ | X 1.71 |
| 3000 | $4.81 \times 10^6$ | $8.64 \times 10^6$ | X 1.80 |
| 3500 | $4.16 \times 10^6$ | $6.61 \times 10^6$ | X 1.59 |
| 3800 | $2.78 \times 10^6$ | $5.23 \times 10^6$ | X 1.88 |

TABLE 3

Medium Resolution (residence time = approx. 12 ms)

| SV(V) | Hexanol (Counts/sec) | Hexanol + MeOH (Counts/sec) | Gain with addition of MeOH |
|---|---|---|---|
| 0 | $1.96 \times 10^6$ | $2.95 \times 10^6$ | X 1.5 |
| 1000 | $1.83 \times 10^6$ | $2.99 \times 10^6$ | X 1.64 |
| 1500 | $1.81 \times 10^6$ | $3.81 \times 10^6$ | X 2.10 |
| 2000 | $1.46 \times 10^6$ | $4.31 \times 10^6$ | X 2.94 |
| 2500 | $1.04 \times 10^6$ | $3.00 \times 10^6$ | X 2.89 |
| 3000 | $6.21 \times 10^5$ | $1.75 \times 10^6$ | X 2.82 |
| 3500 | $1.61 \times 10^5$ | $4.74 \times 10^5$ | X 2.94 |
| 3800 | $4.53 \times 10^4$ | $1.95 \times 10^5$ | X 4.30 |

TABLE 4

High Resolution (residence time = approx. 18 ms)

| SV(V) | Hexanol (Counts/sec) | Hexanol + MeOH (Counts/sec) | Gain with addition of MeOH |
|---|---|---|---|
| 0 | $9.36 \times 10^4$ | $1.34 \times 10^5$ | X 1.43 |
| 1000 | $7.78 \times 10^4$ | $1.60 \times 10^5$ | X 2.05 |
| 1500 | $5.72 \times 10^4$ | $1.80 \times 10^5$ | X 3.15 |
| 2000 | $2.15 \times 10^4$ | $1.09 \times 10^5$ | X 5.10 |
| 2500 | $6.51 \times 10^3$ | $5.32 \times 10^4$ | X 8.18 |
| 3000 | $1.09 \times 10^3$ | $9.39 \times 10^3$ | X 9.05 |
| 3500 | $2.74 \times 10^2$ | $3.51 \times 10^2$ | X 1.28 |

Tables 2, 3 and 4 show signals for bradykinin across all SV settings and low, medium and high resolution, respectively. As is evident, the addition of a methanol solvating modifier had the biggest effect at the highest resolution settings (longest residence times). The maximum gains observed were 1.88×, 4.30× and 9.05× when analyzing bradykinin at low, medium and high resolution, respectively.

Small Molecules

A mixture of 16 small molecules comprising acyclovir, clenbuterol, clomipramine, desipramine, diphenylhydrazine, ketamine, maprotiline, minoxidil, methadone, methylhistamine, norfentanyl, penbutolol, pheniramine, propafenone, terbutaline, and terfanadine was analyzed by multiple reaction monitoring (MRM) in a DMS-MS system.

Figure 12:
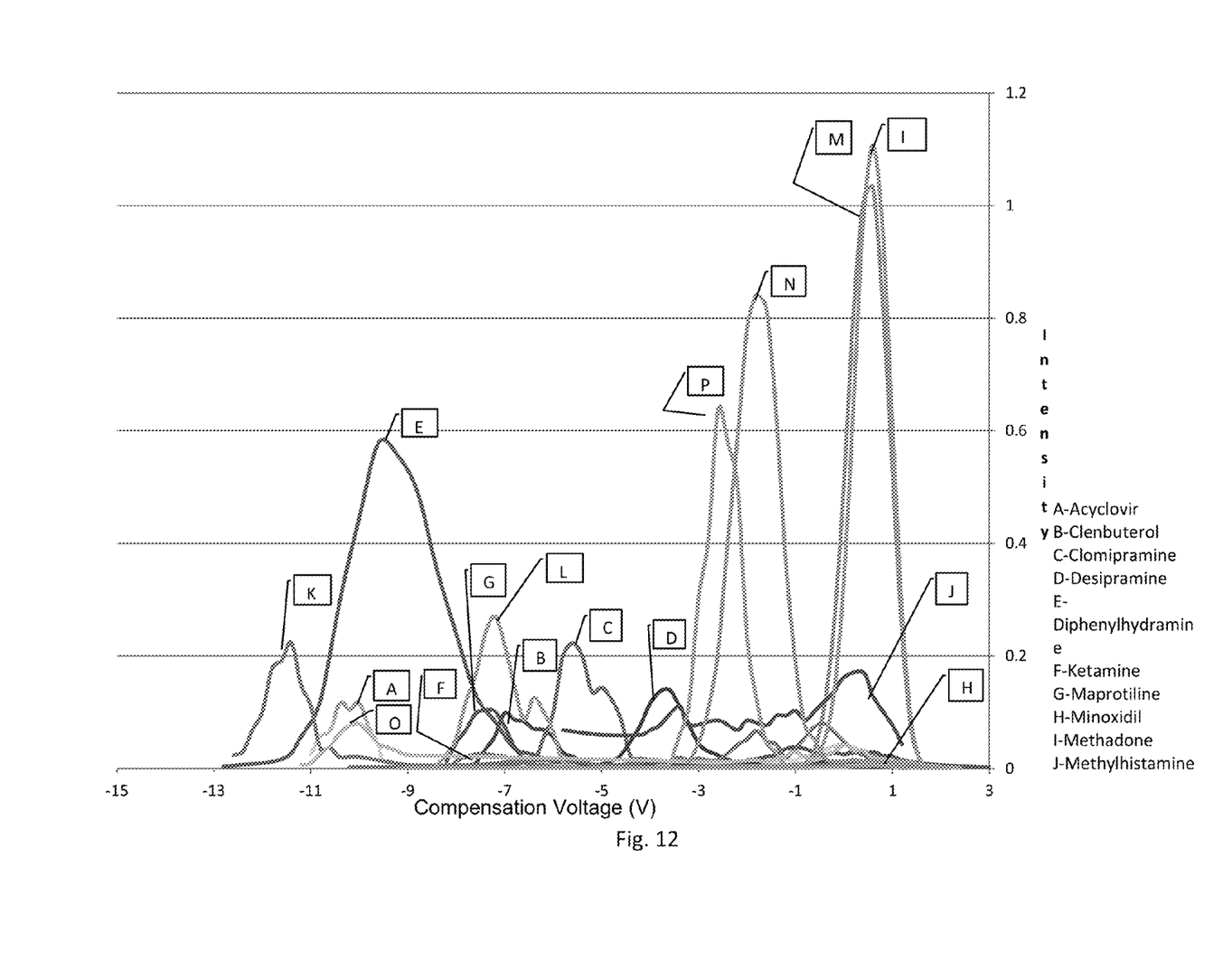
FIG. 12 is an ionogram of a 16 compound mixture using a drift gas modifier mixture that comprises hexanol and cyclohexane.
Figure 13:
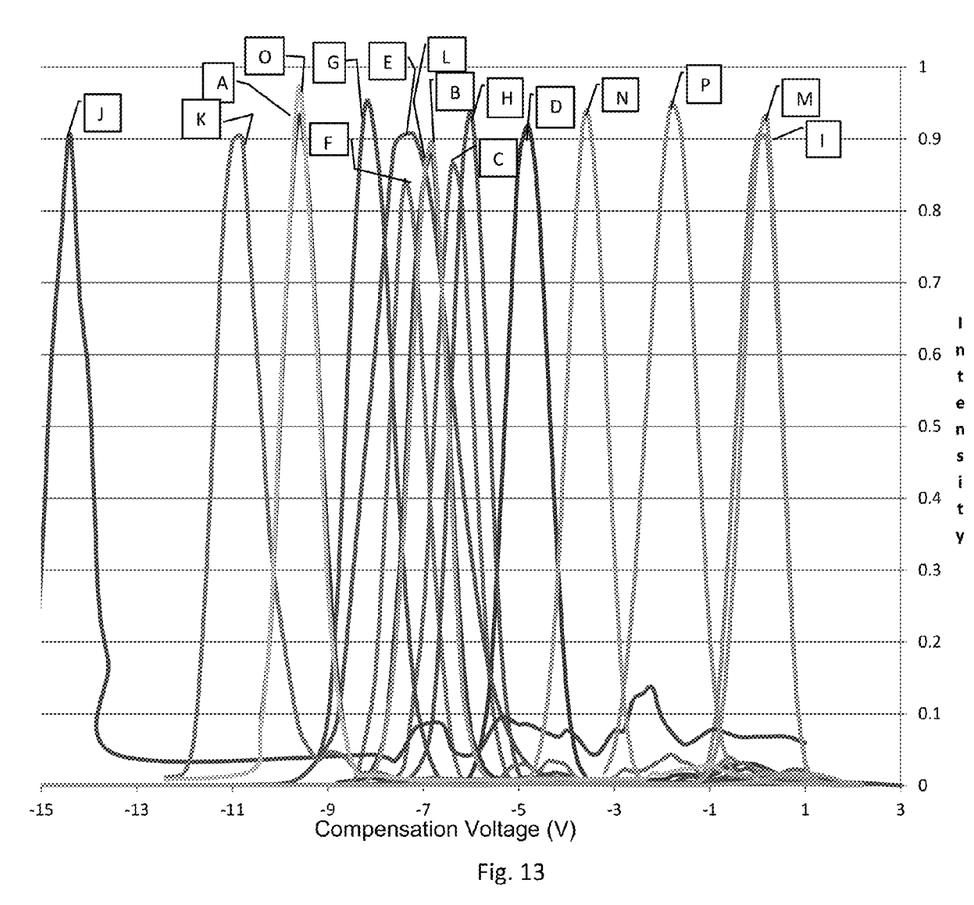
FIG. 13 is an ionogram of a 16 compound mixture using a drift gas modifier mixture that comprises hexanol and methanol.

FIGS. 12 and 13 show a comparison of separations with a separation voltage of 2000V for a modifier mixture comprising 0.13% hexanol, 1.5% cyclohexane, and 0.05% chloroform (FIG. 12) and a modifier mixture comprising 0.13% hexanol, 2% methanol and 0.05% chloroform (FIG. 13). The data are presented as smoothed and normalized ionograms of the small molecule mixture under medium resolution settings and the ion signal for each compound is normalized against the non-smoothed maximum with the second modifier mixture referred to above that comprises methanol.

The solvation energy for methanol is approximately −32 kcal/mol and for cyclohexane is only approximately −10 kcal/mol. Comparing the results from FIGS. 12 and 13, it is apparent that the addition of a methanol solvating modifier, having a lower solvation energy in place of cyclohexane, provides dramatic improvements in signal for the compounds. These improvements are believed to be due to decreased proton transfer and/or possible fragmentation.

Increase in Selectivity

A 15 peptide BSA digest was analyzed in a DMS system wherein chloroform was added as an arc-suppressant modifier. Without the arc-suppressant modifier, the highest separation voltage found that allowed an ionogram to be obtained for the given system was 4000V. With the use of 0.05% chloroform as the arc suppressant modifier, an ionogram could be obtained when the separation voltage was increased to 4250V. At 4250V, an approximate 20% increase in peak capacity was realized over that obtained at 4000V.

In analyzing an eight component sample in a DMS system, with increasing concentrations of chloroform utilized together with a separation isopropanol modifier, higher separation voltages up to the maximum possible (4900 V) could be utilized prior to observing an electric discharge as shown in Table 5.

TABLE 5

Chloroform Modifier and Electric Discharge Observation

| % Chloroform | Voltage at which Discharge Observed |
|---|---|
| 0 | 4100 V |
| 0.07 | 4650 V |
| 0.29 | 4650 V |
| 0.73 | 4850 V |
| 1.46 | No Discharge Observed |

Figure 16:
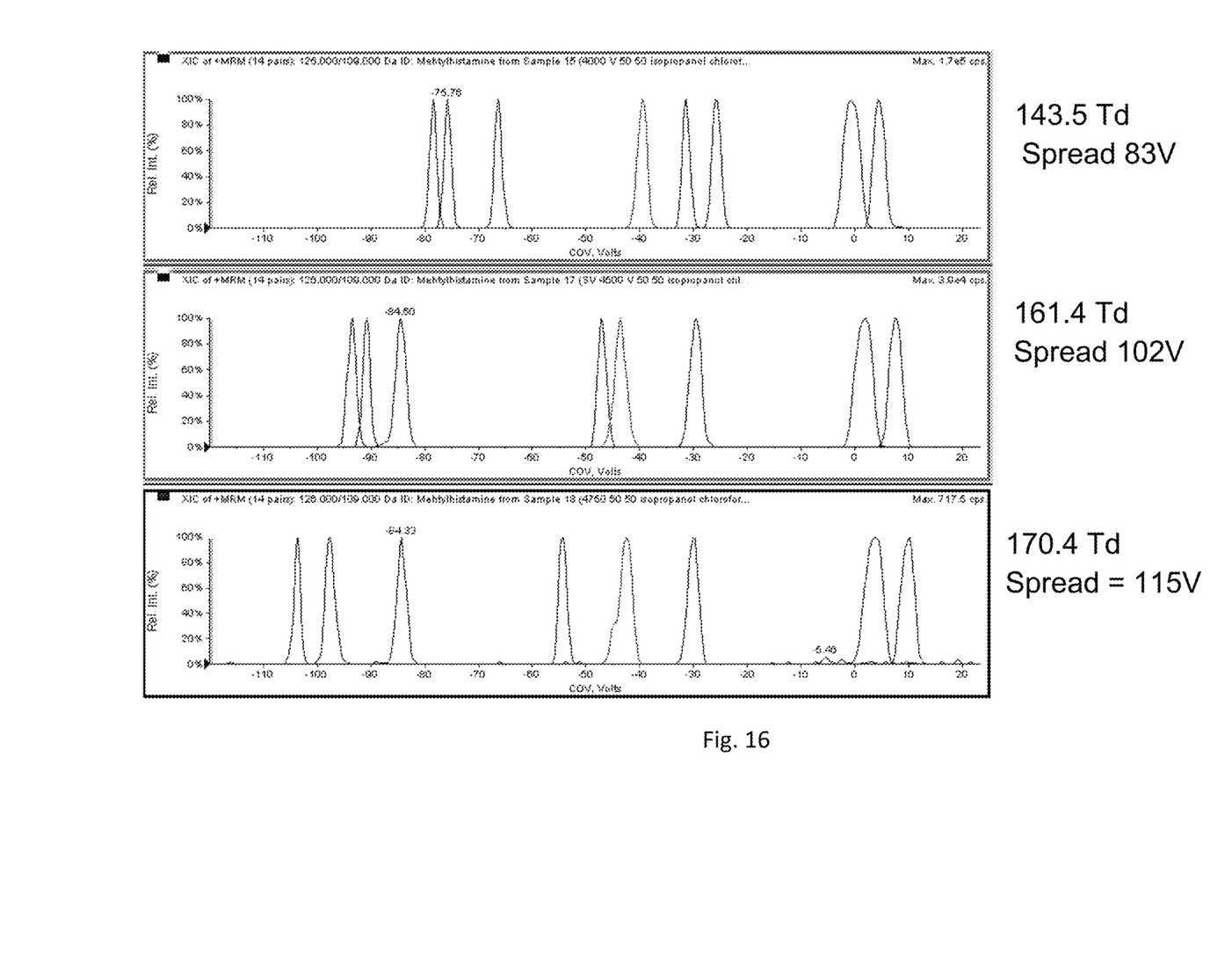
FIG. 16 is an illustration of the increase in selectivity obtained by usage of the within teachings.

FIG. 16 depicts an example of the improvement in peak resolution that is obtained by the usage of higher voltages within the DMS system that result when increasing concentrations of chloroform are utilized with an isopropanol separation modifier. The increased spread of the peaks across the compensation voltage space provides improved peak capacity in addition to resolution improvements.

All literature and similar material cited in this application, including, but not limited to, patents, patent applications, articles, books, treatises, and web pages, regardless of the format of such literature and similar materials, are expressly incorporated by reference in their entireties for all purposes. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

While the applicants' teachings are described in conjunction with various embodiments, it is not intended that the applicant's teachings be limited to such embodiments. On the contrary, the applicants' teachings encompass various alternatives, modifications, and equivalents, as will be appreciated by those of skill in the art.

The teachings should not be read as limited to the described order or elements unless stated to that effect. It should be understood that various changes in form and detail may be made without departing from the scope of the present teachings. By way of example, any of the disclosed method steps can be combined with any of the other disclosed steps to provide a method of analyzing compounds in accordance with various embodiments of the present teachings. Therefore, all embodiments that come within the scope and spirit of the present teachings and equivalents thereto are claimed.

The invention claimed is:

1. A method of utilizing a differential mobility spectrometer or a field asymmetric waveform ion mobility spectrometer, comprising:
    performing a first differential mobility or field asymmetric waveform ion mobility analysis of a sample at a first separation voltage,
    detecting an electric discharge taking place within the differential mobility spectrometer or field asymmetric waveform ion mobility spectrometer,
    wherein after detection of an electric discharge taking place, performing a second differential mobility or field asymmetric waveform ion mobility analysis of the sample at a second separation voltage wherein the second separation voltage is the same or higher than the first separation voltage,
    wherein the second differential mobility of field asymmetric waveform ion mobility analysis is performed by introducing a liquid modifier into a drift gas of the differential mobility spectrometer or the field asymmetric waveform ion spectrometer wherein the liquid modifier comprises an arc-suppressant modifier,
    determining whether an electric discharge takes place during the second differential mobility or field asymmetric waveform ion mobility analysis.

2. The method of claim 1 wherein the arc-suppressant modifier is operable to accept electrons.

3. The method of claim 1 wherein the arc-suppressant modifier is non-polar.

4. The method of claim 1 wherein the arc-suppressant modifier is chloroform.

5. The method of claim 1 wherein the first differential mobility or field asymmetric waveform ion mobility analysis is performed by introducing a liquid modifier into a drift gas of the differential mobility spectrometer or a field asymmetric waveform ion spectrometer, wherein the liquid modifier is a C1 to C10 alcohol.

6. The method of claim 1 further comprising increasing an amount of the arc suppressant modifier at the second separation voltage until an electric discharge is found to not take place.

7. The method of claim 1 wherein the sample comprises a protein, a peptide, an amino acid, or a mixture thereof.

8. The method of claim 1 wherein the sample is comprised of small molecules.

* * * * *